United States Patent [19]
Lai

[11] Patent Number: 5,885,842
[45] Date of Patent: Mar. 23, 1999

[54] METHODS FOR THE DETECTION OF NITRIC OXIDE IN FLUID MEDIA

[75] Inventor: Ching-San Lai, Encinitas, Calif.

[73] Assignee: Medinox, Inc., San Diego, Calif.

[21] Appl. No.: 745,678

[22] Filed: Nov. 8, 1996

[51] Int. Cl.$^6$ .......................... G01N 33/50; G01N 21/00
[52] U.S. Cl. ............................ 436/116; 436/68; 436/118; 436/165; 436/167; 436/168; 422/68.1
[58] Field of Search .................................. 422/116, 68.1, 422/83, 88; 436/165, 167, 168, 116, 118, 68

[56] References Cited

U.S. PATENT DOCUMENTS 5,358,703  10/1994  Lai ............................................ 424/9.33

OTHER PUBLICATIONS

Lewis R, et al, (1993) Membrane mass spectrometer inlet for quantitation of nitric oxide. Biol.Mass.Spectrom. 22:45–52, 1993.

Bredt and Snyder, "Nitric Oxide: A Physiologic Messenger Molecule" *Ann. Rev. Biochem.*, 63: 175–195 (1994).

Bodis and Haregewoin, "Evidence for the Release and Possible Neural Regulation of Nitric Oxide Human Saliva" *Biochem. Biophys. Res. Commun.*, 194(1), 347–350, (1993).

Downes et al., "Determination of a Non–volatile Nitrosamine by Using Denitrosation and a Chemiluminescence Analyser" *Analyst*, 101: 742–748 (1976).

Hibbs et al., "Evidence for Cytokine–inducible Nitric Oxide Synthesis from L–Arginine in Patients Receiving Interleukin–2–Therapy" *J. Clin. Invest.*, 89: 867–877 (1992).

Ignarro, L.J., "Biosynthesis and Metabolism of Endothelium–Derived Nitric Oxide" *Ann. Rev. Toxicol.*, 30: 535–560 (1990).

Ignarro et al., "Endothelium–derived relaxing factor produced and released from artery and vein is nitric oxide" *Proc. Natl. Acad. Sci., USA*, 84: 9265–9269 (1987).

Kelm and Schrader, "Control of Coronary Vascular Tone by Nitric Oxide" *Cir. Res.*, 66(6): 1561–1575 (1990).

Lancaster and Hibbs, "EPR demonstration of iron–nitrosyl complex formation by cytotoxic activated macrophages" *Proc. Natl. Acad. Sci. USA*, 87: 1223: 1227 (1990).

Lowenstein and Snyder, "Nitric Oxide, A Novel Biologic Messenger" *Cell*, 70: 705–707 (1992).

Miles et al., "Association between biosynthesis of nitric oxide and changes in immunological and vascular pararmeters in patients treated with interleukin–2" *Eur. J. Clin. Invest.*, 24: 287–290 (1994).

Moncada, S., "The 1991 Ulf von Euler Lecture The L–arginine:nitric oxide pathway" *Acta Physiol. Scand.*, 145: 201–227 (1992).

Palmer, R. M. J., "The Discovery of Nitric Oxide in the Vessel Wall A Unifying Concept in the Pathogenesis of Sepsis" *Arch. Surg.*, 128: 396–401 (1993).

Palmer et al., "Nitric oxide release accounts for the biological activity of endothelium–derived relaxing factor" *Nature (London)*, 327: 524–526 (1987).

Radomski and Moncada, "Regulation of Vascular Homeostasis by Nitric Oxide" *Thromb. Haemos.*, 70(1): 36–41 (1993).

Robb, W. L., "Thin Silicone Membranes—Their Permeation Properties and Some Aplications" *Ann. N.Y. Acad. Sciences*, 146: 119–137 (1968).

Rodeberg et al., "Nitric Oxide: An Overview" *Am. J. Surg.*, 170: 292–303 (1995).

Shinobu et al., "Sodium N–Methyl–D–glucamine Dithiocarbamate and Cadmium Intoxication" *Acta Pharmacol et Toxicol.*, 54: 189–194 (1984).

Tamir et al., "The Influence of Delivery Rate on the Chemistry and Biological Effects of Nitric Oxide" *Chem. Res. Toxicol.*, 6: 895–899 (1993).

Tannenbaum et al., "The Effect of Nitrate Intake on Nitrite Formation in Human Saliva" *Fd. Cosmet. Toxicol.*, 14: 549–552 (1976).

Vallance et al., "Direct measurement of nitric oxide in human beings" *Lancet*, 346: 153–154 (1995).

*Primary Examiner*—Lora M. Green
*Assistant Examiner*—Joseph W. Ricigliano
*Attorney, Agent, or Firm*—Gray Cary Ware & Freidenrich; Stephen E. Reiter

[57] ABSTRACT

Non-invasive methods have been developed for the measurement of NO levels in a variety of fluid media, e.g., body fluids. The present invention embraces the use of a semipermeable vessel wherein said vessel contains an NO reacting substance to trap NO diffusing thereinto, and a simple physical or chemical detection method to measure the levels of the end products. Since NO is a neutral gas molecule, it is capable of diffusing freely across a wide range of biocompatible polymer membranes which exhibit a high permeability to NO and other neutral gas molecules, such as $O_2$ and $CO_2$, but which are not permeable to charged molecules, such as $NO_3^-$ or $NO_2^-$. The latter two compounds are ubiquitously present in body fluids and often interfere with the measurement of NO levels. The permeability of selected membranes to NO, but not to $NO_3^-$ or $NO_2^-$, makes it possible for the bags employed in the practice of the invention to selectively collect NO, even in the presence of potentially competing species. The simple, easy and non-invasive methods of the invention will find a variety of uses, e.g., for diagnosis and monitoring of NO overproduction (and underproduction) that has been associated with many inflammatory and infectious diseases.

30 Claims, 2 Drawing Sheets

METHODS FOR THE DETECTION OF NITRIC OXIDE IN FLUID MEDIA

FIELD OF THE INVENTION

The present invention relates to methods for the detection of nitric oxide in fluid media, e.g., mammalian body fluids, as well as articles and reagents useful therefor. In one aspect, the present invention relates to non-invasive methods for the detection of nitric oxide in body fluids. In another aspect, the present invention relates to articles useful for collection and detection of nitric oxide in a variety of fluid media. In yet another aspect, the present invention relates to methods to monitor patients for underproduction or overproduction of nitric oxide.

BACKGROUND OF THE INVENTION

Nitric oxide (NO), a gaseous free radical, was once considered mainly as an environmental pollutant from car exhausts and in city smog and cigarette smoke. This view toward nitric oxide was changed in 1987, the year in which NO was discovered to be produced in humans (see, for example, Ignarro et al., in *Proc. Natl. Acad. Sci., USA*, 84:9265–69 (1987) and Palmer et al., in *Nature*, 327:524–26 (1987)). First identified as an endothelium-derived relaxation factor, NO is now recognized as a new kind of cell signaling molecule that regulates the functions of many mammalian cells and tissues.

NO is generated by the enzymatic cleavage of L-arginine, catalyzed by the nitric oxide synthase enzyme (NOS; see, for example, Rodeberg et al., in *Am. J. Surg.*, 170:292–303 (1995), and Bredt and Snyder in *Ann. Rev. Biochem.*, 63:175–95 (1994)). Three different isoforms of NOS have been isolated, cloned, sequenced and expressed, i.e., endothelial cell derived nitric oxide synthase (eNOS), neuronal cell derived nitric oxide synthase (nNOS) and inducible nitric oxide synthase (iNOS). The eNOS and nNOS isoforms are expressed constitutively, and both enzymes require an increase in intracellular calcium for activation. Under physiological conditions, a low output of NO is continuously produced by the eNOS isoform, which is present in numerous cells, including endothelium and neurons. This low level of nitric oxide is involved in a variety of regulatory processes, e.g., blood vessel homeostasis, neuronal communication and immune system functions.

On the other hand, under pathophysiological conditions, a high output of NO is produced by the inducible, calcium-independent NOS isoform (iNOS), which is expressed in numerous cell types, including endothelial cells, smooth muscle cells and macrophages, upon activation with cytokines or endotoxin. These high levels of nitric oxide production (by cytokine-activated macrophages) contribute to, in part, the ability of these cells to kill bacteria or tumor cells and hence play an important role in host defense. However, while excessive NO helps destroy invading microbes, the systemic overproduction of NO by numerous types of cytokine-activated cells, including endothelial cells, smooth muscle cells, macrophages and hepatocytes, may trigger a cascade of events that can result in a variety of inflammatory and infectious diseases and conditions, such as tissue injury, shock, multiple organ failure and death. In fact, abnormally elevated levels of nitric oxide have recently been associated with many inflammatory and infectious diseases or conditions, such as, for example, septic shock, over expression of cytokines, diabetes, allograft rejection, inflammatory bowel disease, rheumatoid arthritis, stroke, multiple sclerosis, and the like.

Similarly, production of an insufficient amount of nitric oxide is also capable of causing a variety of disease states, such as, for example, neonatal persistent pulmonary hypertension, pre-eclampsia, adult respiratory distress syndrome, post-angioplasty restenosis, impotence, and the like.

Nitric oxide is a potent vasodilator (see, for example, Palmer in *Arch. Surg.*, 128:396–401 (1993) and Radomski & Moncada in *Thromb. Haemos.*, 70: 36–41 (1993)). For example, in blood, NO produced by the endothelium diffuses isotropically in all directions into adjacent tissues. As NO diffuses into the vascular smooth muscle, it binds to guanylate cyclase enzyme, which catalyzes the production of cGMP, inducing vasodilation (see, for example, Ignarro, L. J., *Ann. Rev. Toxicol.* 30:535–560 (1990); Moncada, S., *Acta Physiol. Scand.*, 145:201–227 (1992); and Lowenstein and Snyder, *Cell*, 70:705–707 (1992)).

The overproduction of nitric oxide causes an extreme drop in blood pressure, resulting in insufficient tissue perfusion and organ failure, syndromes that are associated with many diseases and/or conditions (e.g., septic shock, stroke, over expression of cytokines, allograft rejection, and the like). The overproduction of nitric oxide is triggered by a number of stimuli, such as the overproduction of inflammatory cytokines (e.g., the overproduction of interleukin-1, interferons, endotoxin, and the like). Additionally, the overproduction of NO has been found to be one of the major side-effects of cytokine therapy (see, for example, Miles et al., in *Eur. J. Clin. Invest.*, 24:287–290 (1994) and Hibbs et al., in *J. Clin. Invest.*, 89:867–877 (1992)). Thus, abnormally elevated nitric oxide levels have been associated with many inflammatory and infectious diseases.

The half-life of NO in vivo is only 3–5 seconds, a short lifetime that makes it very difficult to detect and quantify. Several biophysical techniques have been developed for the measurement of NO levels in aqueous solution. These include chemiluminescence assay (see, for example, Downes et al., *Analyst*, 101:742–748 (1976)), oxyhemoglobin assay (see, for example, Kelm and Schrader, *Cir. Res.*, 66:1561–1575 (1990)), GC-MS detection (see, for example, Palmer et al., *Nature* (London), 327:524–526 (1987)), and nitrosyl-hemoglobin formation detected by electron paramagnetic resonance (EPR) spectroscopy at liquid nitrogen temperature (see, for example, Lancaster et al., *Proc. Natl. Acad. Sci. USA*, 87:1223:1227 (1990)).

Production of NO can also be indirectly detected by measuring its end products, $NO_2^-/NO_3^-$ (see, for example, Palmer et al., supra). None of these techniques in their present form, however, can be used for in vivo detection of NO production. Recently, an invasive electrochemical microsensor to detect NO levels in blood vessels of healthy human volunteers has been described (see, for example, Vallance et al., *Lancet*, 346:153–154 (1995)).

Dithiocarbamates are a class of low molecular-weight sulphur-containing compounds that are effective chelators (see, for example, Shinobu et al., *Acta Pharmacol et Toxicol.*, 54:189–194 (1984)). For example, diethyldithiocarbamate (DETC) is used clinically for the treatment of nickel poisoning. Recently, it was found that N-methyl-D-glucamine dithiocarbamate (MGD) chelates with ferrous iron as a two-to-one [(MGD)$_2$—Fe] complex, which in turn interacts strongly with NO, forming a stable and water-soluble complex in aqueous solution, i.e., [(MGD)$_2$—Fe—NO] (see, for example, Lai & Komarov, *FEBS Lett.*, 345:120–124 (1994)). The latter complex gives rise to a sharp three-line spectrum with $g_{iso}$=2.04, characteristic of a nitrosyl-Fe-dithiocarbamate complex which can readily be detected by EPR spectroscopy at ambient temperatures. This method of detecting NO in body fluids in real time has recently been described by Lai in U.S. Pat. No. 5,358,703.

There is, however, still a need in the art for more rapid, preferably non-invasive methods for the detection of nitric oxide in fluid media such as mammalian body fluids.

BRIEF DESCRIPTION OF THE INVENTION

In accordance with the present invention, non-invasive methods have been developed for the measurement of NO levels in a variety of fluid media, e.g., in mammalian body fluids. The present invention embraces the use of a semi-permeable membrane bag containing a nitric oxide reacting substance (e.g., [(MGD)$_2$—Fe]) to trap NO diffusing into the bag, and a simple physical or chemical detection method to measure the levels of [(MGD)$_2$—Fe—NO] or other end products in the bag.

Since NO is a neutral gas molecule, it is capable of diffusing freely across a wide range of biocompatible polymer membranes, such as polydialkylsiloxane (silicone rubber), polyisoprene and polybutadiene (see, for example, Robb, in Ann. N. Y. Acad. Sciences, 146, 119–137, 1968). Among all polymer membranes, the silicone membrane exhibits a higher permeability to nitric oxide and other neutral gaseous molecules, such as oxygen and carbon dioxide, but is not permeable to charged molecules, such as nitrate ($NO_3^-$) or nitrite ($NO_2^-$) in aqueous solution (see, for example, Tamir et al., in Chem. Res. Toxicol., 6, 895–899, 1993). The latter two compounds, nitrate and nitrite are ubiquitously present in body fluids, such as saliva, blood and urine, and often interfere with the measurement of authentic NO levels. The unique property of a high permeability to nitric oxide but not to nitrate/nitrite makes the silicone membrane an excellent choice for the design of semi-permeable membrane bags employed in the practice of the present invention.

While it has been reported previously that NO was detectable in human saliva, NO levels were assessed by measuring the nitrate/nitrite levels in the saliva using the Griess reaction (see, for example, Bodis and Haregewoin, in Biochem. Biophys. Res. Commun., 194, 347–350, 1993). Since it is well known that human saliva contains high levels of nitrate/nitrite, which vary among individuals according to their health conditions, diet and other factors (see, for example, Tannenbaum et al., in Fd. Cosmet. Toxicol., 14, 549–552, 1976), the measurement of nitrate/nitrite levels in saliva therefore can not be extrapolated to the measurement of authentic NO levels in human saliva. In contrast, in accordance with the present invention, the use of a vessel containing a semi-permeable membrane, which is freely permeable to NO (but not permeable to nitrate/nitrite), prevents contaminants such as nitrate/nitrite from entering the invention vessel, thereby allowing the measurement of authentic NO levels in saliva as well as other body fluids and other fluid media.

For clinical diagnostic use, for example, an invention vessel containing an appropriate NO trapping agent can conveniently be placed underneath the tongue of a patient or such vessel can be surgically introduced subcutaneously. The NO trapping agent contained within the vessel is exposed for a suitable length of time to NO-containing media, and the NO contained in the media trapped, then measured ex vivo. The simple, easy and non-invasive methods of the invention for measurement of NO levels in fluid media will find a variety of uses, e.g., for diagnosis and monitoring of NO overproduction (and underproduction) that has been associated with many inflammatory and infectious diseases.

BRIEF DESCRIPTION OF THE FIGURES

FIG. 1 presents EPR spectra of the [(MGD)$_2$—Fe—NO] complex at 22° C. A silicone membrane bag (with dimensions of 2 cm×2 cm×0.025 cm) containing two opening ports made of silicone tubing (4 cm long with 3 mm o.d. and 1 mm i.d.) on the same side was filled with 0.5 ml of an aqueous solution containing 20 mM MGD and 4 mM ferrous sulfate.

Figure 1A:
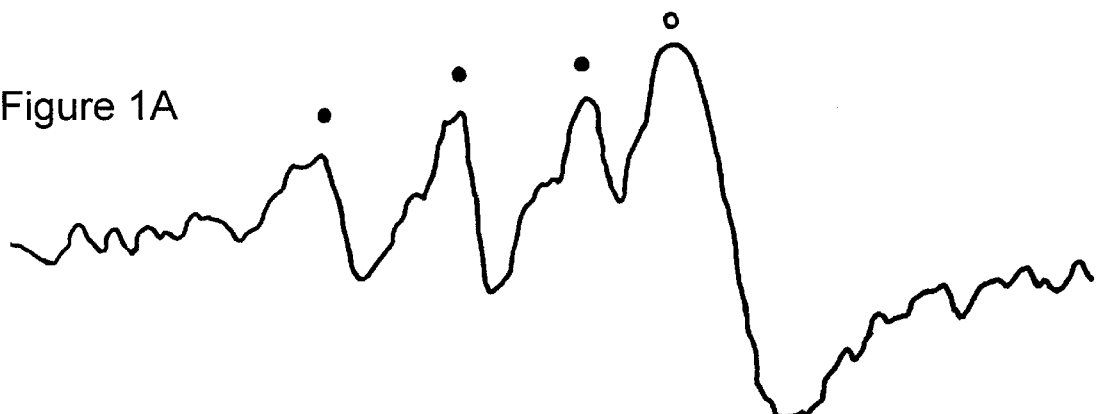
FIG. 1A presents results when the bag was placed underneath the tongue of a human volunteer for one hour, then the contents thereof analyzed for uptake of NO.
Figure 1B:
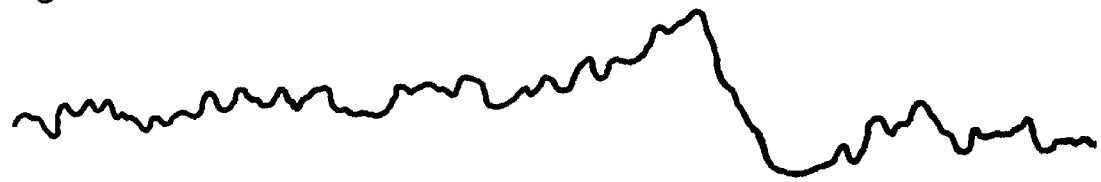
FIG. 1B presents results when the bag was left on the laboratory bench for one hour, then the contents thereof analyzed for uptake of NO.
Figure 1C:
FIG. 1C presents results when the bag was immersed into a 100-ml beaker containing 50 ml of 1 mM nitrite for one hour, then the contents thereof analyzed for uptake of NO.

The spectra referred to in each of FIGS. 1A, 1B and 1C were recorded with an EPR spectrometer, equipped with an X-band microwave bridge and a TE102 cavity, operating at 9.5 GHz. After one hour, the samples were transferred into a quartz EPR flat cell for EPR measurement at room temperature. Instrument settings include 200 G scan range, 0.5 sec time constant, 2.5 G modulation amplitude, 100 kHz modulation frequency and 100 mW microwave power.

Figure 2:
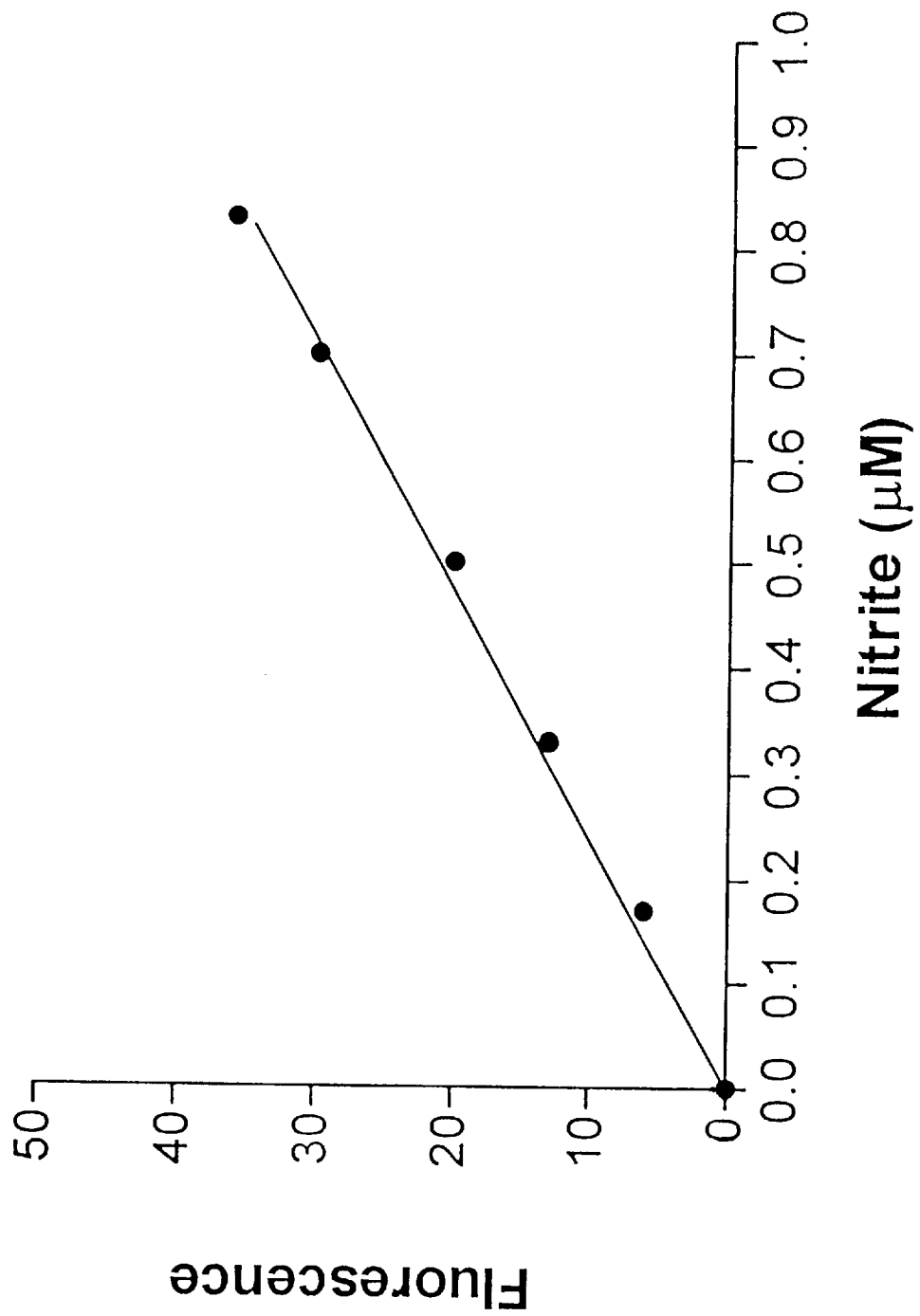

FIG. 2 illustrates the linear relationship between the nitrite levels and fluorescence intensity. An aliquot of 2,3-diaminonaphthalene (DAN) solution at a concentration of 0.2 mg/ml in 0.62N HCl was added to a serial titration of nitrite solution in water with various concentrations ranging from 0 to 1 $\mu$M. The reaction proceeded for 30 min at 22° C. and was then stopped by adding an aliquot of 1N NaOH solution. The fluorescent intensities of the samples were measured by using a fluorescence detection method (Fluoro-Tech 2001A model). Instrument settings included 100 sensitivity, high damping and voltage of 450 V.

DETAILED DESCRIPTION OF THE INVENTION

In accordance with the present invention, there are provided methods for the detection of nitric oxide in fluid media. Invention methods comprise:

contacting fluid media with an article comprising a nitric oxide trapping agent substantially contained within a vessel, wherein the contents of the vessel are capable of communicating with fluid media in contact therewith via a semi-permeable membrane, and wherein said contacting is carried out under conditions suitable to allow diffusion of nitric oxide in the fluid media across the semi-permeable membrane, and determining the amount of nitric oxide trapped by the nitric oxide trapping agent.

In accordance with another embodiment of the present invention, there are provided methods for the detection of disease state(s) or condition(s) which induce the overproduction of nitric oxide. Such methods comprise:

contacting fluid media from a subject suspected of suffering such a disease state with an invention article as described herein, wherein said contacting is carried out under conditions suitable to allow diffusion of nitric oxide in the fluid media across the semi-permeable membrane, and determining the amount of nitric oxide trapped by the nitric oxide trapping agent.

Disease states associated with NO overproduction, and therefor contemplated for monitoring and/or treating in accordance with the present invention include septic shock, ischemia, administration of cytokines, over-expression of cytokines, ulcers, inflammatory bowel diseases (e.g., ulcerative colitis or Crohn's disease), diabetes, arthritis, asthma, Alzeimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, inflammation, toxic shock syndrome, gastritis, adult respiratory distress syndrome, cachexia, myocarditis, autoimmune disorders, eczema, psoriasis, heart failure, heart disease, atherosclerosis, dermatitis, urticaria, cerebral ischemia, systemic lupus erythematosus, AIDS, AIDS dementia, chronic neurodegenerative disease, chronic pain, priapism, cystic fibrosis, amyotrophic lateral sclerosis, schizophrenia, neurodegenerative disorders, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), ophthalmic diseases, and the like.

In accordance with yet another embodiment of the present invention, there are provided methods for the detection of disease state(s) which involve the underproduction of nitric oxide. Such methods comprise:

contacting fluid media from a subject suspected of suffering such a disease state with an invention article as described herein, wherein said contacting is carried out under conditions suitable to allow diffusion of nitric oxide in the fluid media across the semi-permeable membrane, and determining the amount of nitric oxide trapped by the nitric oxide trapping agent.

Disease states which have been correlated with the underproduction of nitric oxide include neonatal persistent pulmonary hypertension, pre-eclampsia, adult respiratory distress syndrome, post-angioplasty restenosis, impotence, atherosclerosis, and the like.

In accordance with still another embodiment of the present invention, there is provided an article comprising a nitric oxide trapping agent substantially contained within a vessel, wherein at least a portion of the vessel comprises a semi-permeable membrane, and wherein the contents of the vessel are capable of communicating with fluid media in contact with the vessel via the semi-permeable membrane.

As readily recognized by those of skill in the art, articles according to the invention can be constructed in a wide variety of shapes and sizes. For example, the vessel employed for the construction of the invention article can comprise a flexible bag constructed substantially entirely of the material used for the semi-permeable membrane.

Alternatively, the vessel employed for the construction of the invention article comprises a rigid or semi-rigid substantially non-porous receptacle for the nitric oxide trapping agent, wherein the receptacle has at least one opening therein, and wherein the nitric oxide trapping agent is retained within the receptacle by the semi-permeable membrane.

As yet another alternative, the vessel employed for the construction of the invention article comprises a pouch containing the nitric oxide trapping agent, wherein at least a portion of the nitric oxide trapping agent is in fluid communication, via the semi-permeable membrane, with fluid media contacting the vessel.

As readily recognized by those of skill in the art, articles according to the invention can be virtually any shape or size, e.g., round, oblong, square, rectangular, tubular, spherical, and the like. The actual size selected for a given article will be dictated by such parameters as access to the fluid sample to be analyzed (e.g., suitable to place in a subject's mouth when NO in saliva is to be analyzed), the volume of nitric oxide trapping agent required (which can vary from about 1 $\mu$l up to about 1 ml), and the like. The thickness of an article according to the invention can vary widely, and will typically be dictated by such parameters as the vessel flexibility required to facilitate sample collection, the degree of permeability required, the amount of time available for sample collection, and the like. Typical article thickness falls in the range of about 0.001 cm up to about 0.2 cm.

As readily recognized by those of skill in the art, a variety of materials can be employed for the preparation of the semi-permeable membrane used to prepare the invention article. Any material which is permeable to neutral gas molecules, but is impermeable to charged molecules is suitable for use herein. Exemplary materials which satisfy these criteria include polydiorganosiloxanes, polyolefins, polyalkadienes, polyvinylbenzenes, halogenated polyolefins, halogenated polyalkadienes, polycarbonates, poly(ethylene terephthalate), polyacrylates, polyurethanes, and the like, as well as mixtures of any two or more thereof.

Examples of suitable polydiorganosiloxanes contemplated for use herein include polydialkylsiloxanes (e.g., polydimethylsiloxane, polydiethylsiloxane, and the like), polydiarylsiloxanes (e.g., polydiphenylsiloxane, polyditolylsiloxane, and the like), polyalkylarylsiloxanes (e.g., polymethylphenyl-siloxane, polymethyltolylsiloxane, and the like), polydialkenylsiloxanes (e.g., polydivinylsiloxane), polyalkenylalkylsiloxanes (e.g., polyvinylmethylsiloxane), polyalkenylarylsiloxanes (e.g., polyvinylphenylsiloxane), and the like.

Examples of suitable polyolefins contemplated for use herein include polypropylene, polyisobutylene, poly (propylene-CO-ethylene), poly(isobutylene-CO-isoprene), poly(isobutylene-CO-maleic acid), and the like.

Examples of suitable polyalkadienes contemplated for use herein include polybutadiene, poly(dimethyl butadiene), polyisoprene, and the like.

Examples of suitable polyvinylbenzenes contemplated for use herein include polystyrene, poly(alpha-methyl styrene), poly(butadiene-styrene), poly(allyl alcohol-styrene), poly(divinylbenzene-styrene), poly(maleic acid-styrene), and the like.

Examples of suitable halogenated polyolefins or halogenated polyalkadienes contemplated for use herein include poly(vinyl chloride), polychloroprene, polytrifluorochloroethylene, polytetrafluoroethylene, and the like.

Examples of suitable polyacrylates contemplated for use herein include polyacrylic acid, poly(methyl methacrylate), poly (methyl methacrylate-CO-ethyl acrylate), poly(methyl methacrylate-CO-methacrylic acid), and the like.

The transport of NO into a semi-permeable bag in a solution under steady-state conditions can be expressed as the following equation (Tamir et al., supra):

Rate of NO transport (mol/s)=($\pi$dL/$\delta$) ($\alpha D_{NO}$) ($\Delta P_{NO}$) f where
- πdL/δ represents the surface area of the bag divided by the wall thickness,
- $\alpha D_{NO}$ represents the NO permeability (i.e., the product of the solubility ($\alpha$) and diffusibility ($D_{NO}$) of NO in the membrane,
- $\Delta P_{NO}$ represents the difference in the partial pressure of NO between the body fluid and the bag, and
- the factor f has a value between 0 to 1, depending on the degree of the boundary layer affecting the reduction of NO transport across the membrane.

Assuming a bag of a dimension of 2 cm×2 cm×0.025 cm, the permeability of NO being $5 \times 10^{-12}$ mol cm$^{-1}$s$^{-1}$ cm Hg$^{-1}$, which is similar to that of molecular oxygen, and an f value between 0.3 and 1, the amount of NO transported across the membrane is solely governed by the difference in the partial pressure of NO between the body fluid and the bag.

The partial pressure of NO inside the bag can be markedly reduced by converting NO into a nondiffusible form, either becoming an adduct, such as in [(MGD)$_2$—Fe—NO] or converting into its end products, nitrate or nitrite. By continuously removing free NO inside the bag (thereby reducing the NO partial pressure), NO transport into the bag will always be favored, and not transport out of the bag. The NO trapped in the form of a dithiocarbamate complex (e.g., [(MGD)$_2$—Fe—NO]) can readily be measured by electron paramagnetic resonance (EPR) spectroscopy (see, for example, Lai and Komarov, supra), or the NO converted into the nitrate/nitrite can be easily assayed by simple Griess reaction (Griess, in Ber. Dtsch. Chem. Ges., 12, 426–428, 1879).

A variety of fluid media can be tested employing the invention method. For example, fluid media including body fluids, growth and maintenance media, industrial fluids, ambient air, and the like can be tested.

Examples of body fluids which can be tested employing invention methods include saliva, blood, tears, urine, synovial fluid, peritoneal fluid, and the like.

Examples of growth and maintenance media which can be tested employing invention methods include organ preservation media, tissue culture media, cell culture media, reperfusion media, and the like.

Examples of industrial waste which can be tested employing invention methods include aqueous or non-aqueous media such as, for example, municipal waste, petroleum refinery effluent, organic synthesis media, and the like.

Examples of ambient air which can be tested employing invention methods include atmospheric air, car exhaust, industrial air, and the like.

A variety of nitric oxide trapping agents are suitable for use in the practice of the present invention. Examples include chelating agents, carboxy-2-phenyl-4,4,5,5-tetramethylimidazoline-oxyl-1-oxyl-3-oxide, nitrones, oxygen, thiol compounds, physiologically compatible aqueous media, apolar oxygenated solvents, guanylate cyclase/GTP system, superoxide anion radicals, peroxynitrite, xanthine (hypoxanthine)/xanthine oxidase system, peroxides, superoxide dismutase, antibodies directed against free radical adducts, Griess reagent, and the like.

Exemplary chelating agents contemplated for use herein include metal ion-containing complexes of dithiocarbamates, the hydroxamic acid siderophore ferrioxamine B and derivatives thereof, metal ion-containing complexes of diethylenetriaminepentaacetic acid, hemoglobins, cobalamin (vitamin B12) and derivatives thereof, porphyrins, heme, myoglobins, meso-2,3-dimercaptosuccinic acid, and the like. Metal ions contemplated for use in the above-described metal ion-containing complexes include iron ions, copper ions, cobalt ions, zinc ions, manganese ions, and the like.

Exemplary dithiocarbamates contemplated for use herein include compounds having the structure:

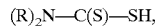

(R)$_2$N—C(S)—SH, wherein each R is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, or the two R groups can cooperate to form a 5-, 6- or 7-membered ring including N and the two R groups.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "acyl" refers to alkyl-carbonyl species.

As employed herein, "halogen" refers to fluoride, chloride, bromide or iodide atoms.

Presently preferred dithiocarbamates contemplated for use in the practice of the present invention are compounds having the structure I, wherein:

one of the R groups is selected from a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, while the other R group is selected from a $C_1$ up to $C_4$ alkyl or substituted alkyl.

Especially preferred dithiocarbamates contemplated for use in the practice of the present invention are compounds having the structure I, wherein:

one of the R groups is selected from a $C_2$ up to $C_8$ alkyl or substituted alkyl, wherein the substituents are selected from carboxyl, acetyl, pyridinyl, pyrrolidinyl, amino, amido, hydroxy or nitro, while the other R group is selected from methyl, ethyl, propyl or butyl.

The presently most preferred dithiocarbamates contemplated for use in the practice of the present invention are compounds having the structure I, wherein:

one of the R groups is selected from a $C_2$ up to $C_8$ alkyl or substituted alkyl, wherein the substituents are selected from carboxyl, acetyl, amido or hydroxy, while the other R group is selected from methyl, ethyl, propyl or butyl.

Exemplary thiol compounds contemplated for use herein include thiol containing amino acids (e.g., cysteine, N-acetyl cysteine, and the like), thiol containing peptides, thiol containing proteins (e.g., albumin, insulin, hemoglobin, lysozyme, immunoglobulins, α-2-macroglobulin, fibronectin, vitronectin, fibrinogen, and the like), glutathione, thiol containing carbohydrates, thiol containing nucleotides, and the like.

Suitable physiologically compatible aqueous media contemplated for use herein as a nitric oxide trapping agent include saline, sterile water, phosphate-buffered saline, culture media, balanced salt solutions, and the like.

Suitable apolar oxygenated solvents contemplated for use herein as a nitric oxide trapping agent include fluorinated cycloaliphatic compounds (e.g., a perfluoroadamantane, a perfluorodecalin, a perfluorohexane, and the like), a fluorinated aromatic compound (e.g., a perfluorobenzene, a perfluorotoluene, and the like), a fluorinated carboxylic acid (e.g., perfluorolauric acid), and the like.

Additional agents useful as nitric oxide trapping agents in the practice of the present invention include superoxide anion radicals, peroxynitrite, xanthine (hypoxanthine)/xanthine oxidase system, peroxides, superoxide dismutase, antibodies directed against free radical adducts, Griess reagent, and the like.

Antibodies directed against free radical adducts contemplated for use herein include antibodies raised against mononitrosyl-metal complexes, S-nitroso proteins (e.g., S-nitrosoalbumin), S-nitrosoglutathione, S-nitroso-L-cysteine, nitrotyrosine-containing proteins and peptides, and the like.

Invention article can be brought into contact with the fluid media to be assayed in any of a variety of ways. For example, the article can be placed under a subject's tongue for a time sufficient to allow diffusion of nitric oxide through the semi-permeable membrane and collection thereof by the nitric oxide trapping agent. Thus the article used in this instance should be of a size and shape which renders it suitable for sublingual introduction into a subject.

Alternatively, the invention article can be surgically introduced into a subject to allow continuous or intermittent detection of nitric oxide levels in various body fluids. Conveniently, the invention article can be subcutaneously introduced into a subject.

As yet another alternative, the invention article can be placed into culture media in cell culture vessels to allow one to monitor the production of nitric oxide by said medium.

The amount of nitric oxide trapped by the invention article can readily be determined in a variety of ways, e.g., by electron paramagnetic resonance spectroscopy, nuclear magnetic resonance, radioisotope tracing, UV-visible spectrophotometry, immunohistchemical methods, fluorescent methods, immunologic methods, gas chromatography, liquid chromatography, thin-layer chromatography, mass spectroscopy, liquid scintillation counting, infrared spectroscopy, and the like.

The invention will now be described in greater detail by reference to the following non-limiting examples.

EXAMPLE 1

EPR detection of NO Production in Human Saliva

A silicone membrane bag filled with an [(MGD)$_2$—Fe] solution (40/8 mM) was placed underneath the tongue of a volunteer. After one hour, the bag was rinsed thoroughly with distilled water, and the solution in the bag was transferred into an EPR quartz flat cell. The X-band EPR measurement was performed at room temperature. As shown in FIG. 1A, an EPR spectrum consisting of two superimposed components, a three-line component (solid circles; $a^N$=12.5 G and $g_{iso}$ =2.04) characteristic of the [(MGD)$_2$—Fe—NO] complex and a strong broad signal (open circle) is obtained. The strong broad signal is part of the EPR spectrum of the [(MGD)$_2$—Cu] complex, suggesting the presence of copper ion in the solution. The concentration of the [(MGD)$_2$—Fe—NO] complex detected in the sample was estimated to be about 5 $\mu$M.

In contrast, when a silicone membrane bag containing the [(MGD)$_2$—Fe] complex was left on the laboratory bench for one hour, no EPR signal of the [(MGD)$_2$—Fe—NO] complex was detectable, as shown in FIG. 1B. Thus, the NO obtained from human saliva, as shown in FIG. 1A, is presumably not due to the presence of NO in the atmospheric air. Additionally, when the silicone membrane bag containing the [(MGD)$_2$—Fe] complex was immersed into a solution containing 1 mM nitrite for one hour, again no EPR signal of the [(MGD)$_2$—Fe—NO] complex was seen, a result indicating that the silicone membrane bag used was not permeable to nitrite. Taken together, the results in FIG. 1 clearly show that the NO trapped by the [(MGD)$_2$—Fe] complex inside the bag was authentic NO present in the human saliva diffusing across the silicone membrane and trapped by the [(MGD)$_2$—Fe] complex. This represents the first unambiguous demonstration of the presence of NO in human saliva.

EXAMPLE 2

Fluorescent Detection of NO Production in Human Saliva

It is known that 2,3-diaminonaphthalene (DAN) reacts with nitrite to form 2,3-naphthotriazole, a fluorophore which can readily be detected and quantified by using fluorescent spectroscopy. A linear relationship between the nitrite levels and fluorescence intensities, as shown in FIG. 2, suggesting that this fluorescence approach is sufficiently sensitive for the measurement of nitrite levels in submicromolar ranges.

NO is known to react with molecular oxygen in aqueous solution to produce nitrite, according to equation (1) presented below. Therefore, measurement of nitrite levels should give a stoichiometric quantitation of the presence of NO in aqueous solution.

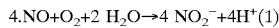

Silicone membrane bags filled with phosphate buffered saline (PBS) solution were placed underneath the tongues of five volunteers. After one hour, the contents in the bags were recovered and assayed for the presence of the nitrite formation by the fluorescent detection with 2,3-diaminonaphthalene. The concentrations of the nitrite in the samples were found to be in the range of 0.5±0.2 $\mu$M. The nitrite levels detected in the samples are due probably to the NO diffused across the silicone membrane and reacted with molecular oxygen (0.25 mM) to form nitrite as shown in the above equation. When the silicone membrane bags filled with PBS solution were immersed into a solution containing 1 mM nitrite for one hour, no fluorescent signal was detected in the samples. The result further confirms the contention that the nitrite detected in the samples was formed via the NO diffused into the bag reacting with oxygen rather than through the nitrite contamination in the saliva.

It is interesting to note that the NO level in the human saliva detected by EPR method was about ten times higher than that detected by the fluorescent method. The difference could be attributed to the nature of NO trapping in these two different systems. In the [(MGD)$_2$—Fe] trapping method, the NO diffusing into the bag reacts rapidly with the [(MGD)$_2$—Fe] to form a nondiffusible [(MGD)$_2$—Fe—NO] complex, a process that further facilitates NO transport because of the reduction of the NO partial pressure inside the bag. On the other hand, in the PBS trapping method, the NO diffusing into the bag reacts with dissolved oxygen at a reaction rate of $10^6$ M$^{-2}$ s$^{-1}$, a reaction rate that is second order with respect to NO and first order with respect to oxygen. This reaction proceeds slowly, which could account for the low trapping efficiency with the PBS trapping system.

While the invention has been described in detail with reference to certain preferred embodiments thereof, it will be understood that modifications and variations are within the spirit and scope of that which is described and claimed.

That which is claimed is:

1. A method for the detection of nitric oxide in liquid media, said method comprising:

providing an article comprising a nitric oxide trapping agent contained within a vessel, wherein the contents of said vessel are capable of communicating with liquid media brought into contact with said vessel via a semi-permeable membrane, wherein said semi-permeable membrane is permeable to neutral gas molecules, but is impermeable to charged molecules, contacting liquid media suspected of containing nitric oxide with said article, wherein said contacting is carried out under conditions suitable to allow diffusion of nitric oxide in said liquid media across the semi-permeable membrane of said article, and determining the amount of nitric oxide trapped by said nitric oxide trapping agent.

2. The method according to claim 1 wherein said liquid media is selected from the group consisting of body fluids, growth media, and industrial fluids.

3. The method according to claim 2 wherein said liquid media is a body fluid selected from the group consisting of saliva, blood, tears, urine, synovial fluid and peritoneal fluid.

4. The method according to claim 2 wherein said liquid media is a growth and maintenance medium selected from the group consisting of organ preservation media, tissue culture media, cell culture media and reperfusion media.

5. The method according to claim 2 wherein said liquid media is aqueous or non-aqueous industrial waste.

6. The method according to claim 1 wherein said nitric oxide trapping agent is selected from the group consisting of chelating agents, carboxy-2-phenyl-4,4,5,5-tetramethylimidazoline-oxyl-1-oxyl-3-oxide, nitrones, oxygen, thiol compounds, physiologically compatible aqueous media, apolar oxygenated solvents, guanylate cyclase/GTP system, superoxide anion radicals, peroxynitrite, xanthine (hypoxanthine)/xanthine oxidase system, peroxides, superoxide dismutase, antibodies directed against free radical adducts and Griess reagent.

7. The method according to claim 6 wherein said chelating agents are selected from the group consisting of metal ion-containing complexes of dithiocarbamates, hydroxamine acid siderophore ferrioxamine B and derivatives thereof, metal ion-containing complexes of diethylenetriaminepentaacetic acid, hemoglobins, cobalamin (vitamin B12) and derivatives thereof, porphyrins, heme, myoglobins and meso-2,3-dimercaptosuccinic acid.

8. The method according to claim 7 wherein said metal ions are iron, copper, cobalt, zinc or manganese ions.

9. The method according to claim 7 wherein said dithiocarbamates is selected from compounds having the structure:

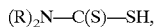

wherein each R is independently a $C_1$ up to $C_{18}$ alkyl, substituted alkyl, cycloalyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, or the two R groups can cooperate to form a 5-, 6- or 7-membered ring including N and the two R groups.

10. The method according to claim 6 wherein said thiol compounds are thiol containing amino acids, thiol containing peptides, thiol containing proteins, glutathione, thiol containing carbohydrates or thiol containing nucleotides.

11. The method according to claim 6 wherein said physiologically compatible aqueous media is selected from the group consisting of saline, sterile water, phosphate-buffered saline, culture media and balanced salt solutions.

12. The method according to claim 6 wherein said apolar oxygenated solvent is a fluorinated cycloaliphatic compound, a fluorinated aromatic compound or a fluorinated carboxylic acid.

13. The method according to claim 6 wherein said nitric oxide trapping agent is selected from the group consisting of superoxide anion radicals, peroxynitrite, xanthine (hypoxanthine)/xanthine oxidase system, peroxides and Griess reagent.

14. The method according to claim 1 wherein said vessel comprises:
- a flexible bag constructed of said semi-permeable membrane; or
- a rigid or semi-rigid receptacle containing said nitric oxide trapping agent, wherein said receptacle has at least one opening therein, and wherein said nitric oxide trapping agent is retained within said receptacle by said semi-permeable membrane; or
- a pouch containing said nitric oxide trapping agent, wherein at least a portion of said nitric oxide trapping agent is in fluid communication with said liquid media via said semi-permeable membrane.

15. The method according to claim 1 wherein said vessel is suitable for sublingual introduction into a subject.

16. The method according to claim 1 wherein said vessel is suitable for subcutaneous introduction into a subject.

17. The method according to claim 16 further comprising surgically introducing said vessel into said subject.

18. The method according to claim 1 wherein said vessel is suitable for placing into culture media in cell culture vessels.

19. The method according to claim 1 wherein said semi-permeable membrane is prepared from one or more materials selected from the group consisting of polydiorganosiloxane, polyolefins, polyalkadienes, polyvinylbenzene, halogenated polyolefins, halogenated polyalkadienes, polycarbonates, poly(ethylene terphthalate), polyacrylates, and polyurethanes.

20. The method according to claim 19 wherein said semi-permeable membrane is prepared from one or more polydiorganosiloxanes selected from the group consisting of polydialkylsiloxane, polydiarylsiloxane, polyalkylarysiloxane, polydialkenylsiloxane, polyalkenylalkylsiloxane and polyalkenylarylsiloxane.

21. The method according to claim 19 wherein said semi-permeable membrane is a polyolefin selected from the group consisting of polypropylene, polyisobutylene, poly(propylene-CO-ethylene), poly(isobutylene-CO-isoprene) and poly(isobutylene-CO-maleic acid).

22. The method according to claim 19 wherein said semi-permeable membrane is a polyalkadiene selected from the group consisting of polybutadiene, poly(dimethyl butadiene) and polyisoprene.

23. The method according to claim 19 wherein said semi-permeable membrane is a polyvinylbenzene selected from the group consisting of polystyrene, poly(alpha-methyl styrene), poly(butadiene-styrene), poly(allyl alcohol-styrene), poly(divinylbenzene-styrene) and poly(maleic acid-styrene).

24. The method according to claim 19 wherein said semi-permeable membrane is a halogenated polyolefin or halogenated polyalkadiene selected from the group consisting of poly(vinyl chloride), polychloroprene, polytrifluorochloroethylene and polytetrafluoroethylene.

25. The method according to claim 19 wherein said semi-permeable membrane is a polyacrylate selected from group consisting of polyacrylic acid, poly(methyl methacrylate), poly(methyl methacrylate-CO-ethyl acrylate) and poly(methyl methacrylate-CO-methacrylic acid).

26. The method according to claim 1 wherein the amount of nitric oxide trapped by said article is determined by electron paramagnetic resonance spectroscopy, nuclear magnetic resonance, radioisotope tracing, UV-visible spectrophotometry, immunohistchemical methods, fluorescent methods, immunologic methods, gas chromatography, liquid chromatography, thin-layer chromatography, mass spectroscopy, liquid scintillation counting or infrared spectroscopy.

27. A method for the detection of disease state(s) or conditions(s) in a subject in whom the overproduction of nitric oxide occurs, said method comprising,
- contacting liquid media from said subject with an article comprising a nitric oxide trapping agent contained within a vessel, wherein the contents of said vessel are capable of communicating with liquid media in contact with said vessel via a semi-permeable membrane, wherein said semi-permeable membrane is permeable to neutral gas molecules, but is impermeable to charged molecules, and wherein said contacting is carried out under conditions suitable to allow diffusion of nitric oxide in said liquid media across said semi-permeable membrane, and
- determining the amount of nitric oxide trapped by said nitric oxide trapping agent.

28. The method according to claim 27 wherein said disease state or condition is septic shock, ischemia, administration of cytokines, over-expression of cytokines, ulcers, inflammatory bowel diseases, diabetes, arthritis, asthma, Alzeimer's disease, Parkinson's disease, multiple sclerosis, cirrhosis, allograft rejection, liver inflammation, encephalomyelitis, meningitis, pancreatitis, peritonitis, vasculitis, lymphocytic choriomeningitis, glomerulonephritis, uveitis, ileitis, renal inflammation, hemorrhagic shock, anaphylactic shock, burn, infection, hemodialysis, chronic fatigue syndrome, stroke, cancers, cardiopulmonary bypass, ischemic/reperfusion injury, inflammation, toxic shock syndrome, gastritis, adult respiratory distress syndrome, cachexia, myocarditis, autoimmune disorders, eczema, psoriasis, heart failure, heart disease, atherosclerosis, dermatitis, urticaria, cerebral ischemia, systemic lupus erythematosus, AIDS, AIDS dementia, chronic neurodegenerative disease, chronic pain, priapism, cystic fibrosis, amyotrophic lateral sclerosis, schizophrenia, neurodegenerative disorders, obesity, gastrointestinal motility disorders, hyperphagia, solid tumors, malaria, hematologic cancers, myelofibrosis, lung injury, graft-versus-host disease, head injury, CNS trauma, hepatitis, renal failure, liver disease, drug-induced lung injury, myasthenia gravis (MG) or ophthalmic diseases.

29. A method for the detection of disease state(s) which involve the underproduction of nitric oxide, said method comprising
- contacting liquid media from a subject suspected of suffering such a disease state with an article comprising a nitric oxide trapping agent substantially contained within a vessel, wherein the contents of said vessel are capable of communicating with liquid media in contact with said vessel via a semi-permeable membrane, and wherein said contacting is carried out under conditions suitable to allow diffusion of nitric oxide in said liquid media across said semi-permeable membrane, and
- determining the amount of nitric oxide trapped by said nitric oxide trapping agent.

30. The method according to claim 29 wherein said disease state is neonatal persistent pulmonary hypertension, pre-eclampsia, adult respiratory distress syndrome, post-angioplasty restenosis, impotence or atherosclerosis.

* * * * *

UNITED STATES PATENT AND TRADEMARK OFFICE
CERTIFICATE OF CORRECTION

PATENT NO. : 5,885,842
DATED : March 23, 1999
INVENTOR(S) : Ching-San Lai

It is certified that error appears in the above-indentified patent and that said Letters Patent is hereby corrected as shown below:

On the title page, item [73] Assignee should read--

Medinox, Inc., San Diego, Calif. and MCW Research Foundation, Milwaukee, Wisc.

Signed and Sealed this

Sixth Day of March, 2001

Attest:

NICHOLAS P. GODICI

*Attesting Officer*      *Acting Director of the United States Patent and Trademark Office*